United States Patent
Bobbio et al.

(10) Patent No.: US 10,130,096 B2
(45) Date of Patent: Nov. 20, 2018

(54) METHOD FOR PROTECTING USEFUL PLANTS OR PLANT PROPAGATION MATERIAL

(71) Applicant: SYNGENTA PARTICIPATIONS AG, Basel (CH)

(72) Inventors: Carla Bobbio, Stein (CH); Christophe Weider, Stein (CH); Ronald Zeun, Stein (CH); Ramya Rajan, Goa (IN); Daniel Stierli, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 14/347,285

(22) PCT Filed: Oct. 8, 2012

(86) PCT No.: PCT/EP2012/069835
§ 371 (c)(1),
(2) Date: Mar. 26, 2014

(87) PCT Pub. No.: WO2013/050591
PCT Pub. Date: Apr. 11, 2013

(65) Prior Publication Data
US 2014/0259230 A1 Sep. 11, 2014

(30) Foreign Application Priority Data

Oct. 7, 2011 (EP) .................................... 11184373
Sep. 14, 2012 (IN) ........................... 2887/DEL/2012

(51) Int. Cl.
*A01N 55/08* (2006.01)
*A01N 25/00* (2006.01)

(52) U.S. Cl.
CPC ............. *A01N 55/08* (2013.01); *A01N 25/00* (2013.01)

(58) Field of Classification Search
CPC ................. A01N 55/08; A01N 25/00
See application file for complete search history.

(56) References Cited

U.S. PATENT DOCUMENTS

| 3,686,398 A | 8/1972 | Kohn et al. |
| 3,873,279 A | 3/1975 | Singer |
| 2010/0267981 A1 | 10/2010 | Baker et al. |

FOREIGN PATENT DOCUMENTS

| WO | 95/33754 A1 | 12/1995 |
| WO | 2006/089067 A2 | 8/2006 |

OTHER PUBLICATIONS

Kumar et al., Tetrahedron Letters, 51, 2010, 4482-4485.
Mao, "AN2690, a topical antifungal agent in development for the treatment of onychomycosis represents a new class and has a novel mechanism of action", Anacor Pharmaceuticals, Inc., Aug. 20, 2008, XP007921849, Retrieved from the Internet: URL:http://web.archive.org/web/20080820044059/http://anacor.com/pdf/SID_P769.pdf.
International Search Report for International Appln. No. PCT/EP2012/069835.

*Primary Examiner* — John Pak
*Assistant Examiner* — Andriae M Holt
(74) *Attorney, Agent, or Firm* — Dinsmore & Shohl LLP; Toni-Junell Herbert

(57) ABSTRACT

A method of controlling phytopathogenic diseases on useful plants or plant propagation material thereof, which comprises applying to said plant or plant propagation material a fungicidally effective amount of a compound of formula (I)

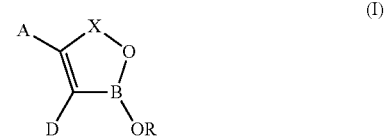

wherein all the substituent save indicated as in claim 1.

12 Claims, No Drawings

METHOD FOR PROTECTING USEFUL PLANTS OR PLANT PROPAGATION MATERIAL

The present invention relates to the method for protecting useful plants or plant propagation material, more specifically to a method use of oxaboroles and salts thereof as biocides in agriculture or horticulture for controlling or preventing infestation of plants or plant propagation material, harvested food crops by phytopathogenic microorganisms, preferably fungi.

The incidence of serious fungal infections, either systemic or topical, continues to increase for plants, animals, and humans. Many fungi are common in the environment and not harmful to plants or mammals. However, some fungi can produce disease in plants, humans and/or animals.

Fungicides are compounds, of natural or synthetic origin, which act to protect plants against damage caused by fungi, including oomycetes. Current methods of agriculture rely heavily on the use of fungicides. In fact, some crops cannot be grown usefully without the use of fungicides. Using fungicides allows a grower to increase the yield of the crop and consequently, increase the value of the crop. Numerous fungicidal agents have been developed. However, the treatment of fungal infestations and infections continues to be a major problem. Furthermore, fungicide and antifungal drug resistance has become a serious problem, rendering these agents ineffective for some agricultural and therapeutic uses. As such, a need exists for the development of new fungicidal and antifungal compounds and inventive uses of known compounds.

The use of oxaboroles and salts thereof as industrial biocides especially fungicides for the protection of plastics materials such as plasticised PVC is know from WO95/33754.

According to the present invention there is provided a method for controlling or preventing infestation of plants or plant propagation material and/or harvested food crops susceptible to microbial attack by treating plants or plant propagation material and/or harvested food crops with an effective amount of an oxaborole of general formula (I)

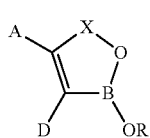

(I)

wherein A and D are each independently, hydrogen, optionally substituted $C_{1-18}$-alkyl, arylalkyl, aryl, or heterocyclic or where A and D together with the carbon atoms to which they are attached form a 5, 6 or 7-membered fused ring which itself may be substituted;

X is a group —$CR^1R^2$ wherein $R^1$ and $R^2$ are each, independently, hydrogen, optionally substituted $C_{1-6}$-alkyl, nitrile, nitro, aryl or arylalkyl or $R^1$ and $R^2$ together with the carbon atom to which they are attached form an alicyclic ring;

R is hydrogen, optionally substituted $C_{1-18}$-alkyl, arylalkyl, aryl, heteroaryl, cycloalkyl or a radical of formula (II)

(II)

wherein A, D and X are as hereinbefore.

The present invention accordingly further relates to the use of oxaboroles derivatives according to formula (I) and salts thereof for controlling or preventing infestation of plants or plant propagation material, the application of oxaboroles derivatives according to formula (I) to useful plants, the application of oxaboroles derivatives according to formula (I) to the locus of useful plants or the application of oxaboroles derivatives according to formula (I) to plant propagation material of useful plants a compound of formula (I).

The present invention accordingly further relates to the use of oxaboroles derivatives according to formula (I) and salts thereof for controlling or preventing infestation of plants or plant propagation material by treating plants or plant propagation material with an effective amount of an oxaborole of general formula (I).

The present invention accordingly further relates to the method of controlling phytopathogenic diseases on useful plants or plant propagation material thereof, which comprises applying to said plant or plant propagation material a fungicidally effective amount of a compound of formula (I). Preferably the method of controlling phytopathogenic diseases on useful plants or plant propagation material thereof, which comprises applying to said plant or plant propagation material a fungicidally effective amount of a compound of formula (I), wherein plant propagation material of useful plants are seeds of useful plants.

The present invention accordingly further relates to the method for controlling or preventing infestation of plants or plant propagation material by treating plants or plant propagation material with an effective amount of an oxaborole of general formula (I).

The present invention accordingly further relates to the method of controlling phytopathogenic diseases on useful plants or plant propagation material thereof, which comprises applying to said plant propagation material a fungicidally effective amount of a compound of formula (I).

Accordingly the present invention also relates to a method of protecting plant propagation material and organs that grow at a later point in time against damage phytopathogenic diseases, which method comprises applying to said propagation material a fungicidally effective amount of a compound of formula I.

In a further aspect of the invention, the invention provides a plant propagation material protecting composition comprising a compound of formula I, together with a suitable carrier therefore.

In a further aspect of the invention, the invention provides a method of controlling phytopathogenic diseases on useful plants or plant propagation material thereof, which comprises applying to said plant propagation material a fungicidally effective amount of a plant propagation material protecting composition comprising a compound of formula (I) as defined in claim 1, together with a suitable carrier therefore.

A preferred embodiment of this aspect of the invention is a plant propagation material protecting composition comprising a compound of formula I, together with a suitable carrier therefor, wherein said plant propagation material protecting composition comprises additionally a colouring agent.

In yet a further aspect of the invention, the invention provides plant propagation material treated with a plant propagation material protecting composition comprising a compound of formula I, together with a suitable carrier therefor.

A preferred embodiment of this aspect of the invention is plant propagation material treated with a plant propagation material protecting composition comprising a compound of formula I, together with a suitable carrier therefor, wherein said plant propagation material protecting composition comprises additionally a colouring agent.

A method of controlling or preventing pest damage in a growing plant said method comprising applying onto the plant propagation material, before planting or sowing thereof a compound of formula (I).

A method of controlling or preventing pest damage in a growing plant or growing plant tissue said method comprising: applying onto the plant propagation material, before planting or sowing thereof a fungicidial effective amount of a compound of formula (I).

A method of controlling or preventing fungal diseases in a growing plant or growing plant tissue said method comprising: applying onto the plant propagation material before planting or sowing thereof a fungicidial effective amount of a compound of formula (I).

In a preferred embodiment the plant propagation material is a seed or a tuber. In a further preferred embodiment the plant propagation material is a seed. In a further preferred embodiment the plant propagation material is a tuber. Preferably the seeds and tubers (stem tubers and root tubers) according to this application are alive. Preferably the seeds and tubers according to this application are able to germinate In a further aspect of the invention, the invention provides a method of controlling or preventing pest damage in a growing plant said method comprising applying onto the seed, before planting or sowing thereof a compound of formula (I).

In a further aspect of the invention, the invention provides a method of controlling or preventing pest damage in a growing plant or growing plant tissue said method comprising: applying onto the seed, before planting or sowing thereof a fungicidial effective amount of a compound of formula (I).

In a further aspect of the invention, the invention provides a method of controlling or preventing fungal diseases in a growing plant or growing plant tissue said method comprising: applying onto the seed before planting or sowing thereof a fungicidial effective amount of a compound of formula (I).

In a further aspect of the invention, the invention provides a method of protecting plant propagation material and organs that grow at a later point in time against damage phytopathogenic diseases, which method comprises applying to said propagation material a fungicidally effective amount of a compound of formula (I).

In a further aspect of the invention, the invention provides a plant propagation material comprising compound a compound of formula (I). Preferably the plant propargation material comprising a fungicidial effective amount of a compound of formula (I).

In a further aspect of the invention, the invention provides a plant propagation material comprising compound a compound of formula (I) and comprises additionally a colouring agent.

In a further aspect of the invention, the invention provides a coated plant propagation material coated with a compound of formula (I).

In a further aspect of the invention, the invention provides a combination of a plant propagation material and a compound of formula (I).

In a further aspect of the invention, the invention provides a coated plant propagation material coated with coating comprising a compound of formula (I) as defined in claim 1.

In a further aspect of the invention, the invention provides a plant propagation material comprising an outer coating characterized that the outer coating comprises a compound according to formula (I), preferably a seed comprising an outer coating characterized that the outer coating comprises a compound according to formula (I).

In a further aspect of the invention, the invention provides a composition comprising a plant propagation material and a compound of formula (I).

In a further aspect of the invention, the invention provides a composition comprising a plant propagation material and a compound of formula and further comprising a seed grow medium.

In a further aspect of the invention, the invention provides a plant which results from the germination of a coated seed wherein the coating comprises a compound of formula (I).

In a further aspect of the invention, the invention provides a coated plant propagation material wherein the coating comprises a compound of formula (I).

In a further aspect of the invention, the invention provides a coated plant propagation material according to the preceding paragraph, wherein the said material is a seed.

In a further aspect of the invention, the invention provides the combination of a plant propagation material and a composition comprising a compound of formula (I).

In a further aspect of the invention, the invention provides the combination according to the preceding paragraph wherein the said material is a seed.

In a further aspect of the invention, the invention provides the combination according to one of the two preceding paragraphs, further comprising a plant growth and/or seed germination medium.

In a further aspect of the invention, the invention provides a plant which results from the germination and/or growth of the coated plant propagation material wherein the coating comprises a compound of formula (I).

In a further aspect of the invention, the invention provides a plant which results from the germination and/or growth of the coated plant propagation material wherein the coating comprises a compound of formula (I) and wherein the coated plant propagation material is a seed. Preferably the coated plant propagation material is a seed.

In a further aspect of the invention, the invention relates to the use of a compound of formula (I) according to claim 1, in the preparation of a composition for coating a plant propagation material for the prevention or control of plant pathogenic fungi.

The compounds of formula I are applied by treating plant propagation material with a fungicidally effective amount of a compound of formula I. Preferably, compounds of formula I are applied by adhering compounds of formula I to plant propagation material in a fungicidally effective amount.

A preferred application method is seed treatment. The

The method according to the invention is especially suitable to increase the yield and/or quality of useful plants, such as crop yield of crop plants.

Accordingly the present invention further relates to a method of improving the growing characteristics of a plant, which method comprises applying to said propagation material a fungicidally effective amount of a compound of formula I.

The invention covers all agronomically acceptable salts, isomers, structural isomers, stereoisomers, diastereoisomers, enantiomers, tautomers and N-oxides of those compounds. The compounds of formula I may exist in different geometric or optical isomeric forms or in different tautomeric forms. One or more centres of chirality may be present, in which case compounds of the formula I may be present as pure enantiomers, mixtures of enantiomers, pure diastereomers or mixtures of diastereomers. There may be double bonds present in the molecule, such as C=C or C=N bonds, in which case compounds of formula I may exist as single isomers or mixtures of isomers. Centres of tautomerisation may be present. This invention covers all such isomers and tautomers and mixtures thereof in all proportions as well as isotopic forms such as deuterated compounds. Also atropisomerism may occur as a result of a restricted rotation about a single bond.

Suitable salts of the compounds of formula I include acid addition salts such as those with an inorganic acid such as hydrochloric, hydrobromic, sulphuric, nitric or phosphoric acid, or an organic carboxylic acid such as oxalic, tartaric, lactic, butyric, toluic, hexanoic or phthalic acid, or a sulphonic acid such as methane, benzene or toluene sulphonic acid. Other examples of organic carboxylic acids include haloacids such as trifluoroacetic acid.

Unless otherwise stated, the substituents or the moieties respectively A, D, X, R, $R^1$, $R^2$, $R^3$, $R^4$, $R^5$ and $R^6$ are unsubstituted or substituted. If the substituents are substituted, the substituents are given below as well.

The alkyl groups, the alkenyl groups, the alkynyl groups and the alkoxy groups in the compound of formula (I) are either linear or branched or they are perhalogenated and forming haloalkyl groups, haloalkenyl groups, haloalkynyl groups or haloalkoxy groups. Halogen signifies preferably F, Cl, Br, I, and more preferred halogen signifies F or Cl. A oxo substituent is =O, thus a oxygen atom doubly bonded to carbon or another element. The term "oxo substituent" thus embraces aldehydes, carboxylic acids, ketones, sulfonic acids, amides and esters.

The preferred substituents of the substituted alkyl groups, the substituted alkenyl groups, the substituted alkynyl groups, the substituted alkoxy groups, substituted aryl groups and/or the aromatic heterocycle groups in the compound of formula (I) are selected from the following substituents F, Cl, Br, I, —OH, —CN, nitro, a oxo substituent, —$C_{1-4}$alkoxy, —$C_{1-4}$ alkylthio, $C_{1-4}$alkyl, $C_{2-4}$alkenyl, $C_{2-4}$alkenyl, $C_{2-4}$alkynyl, —C(O)H, —C(O)($C_{1-4}$ alkyl), —C(O)($C_{1-4}$ alkoxy), —C(O)$NH_2$, —C(O)NH($C_{1-4}$ alkyl), —C(O)N($C_{1-4}$ alkyl)($C_{1-4}$ alkyl), —OC(O)NH($C_{1-4}$ alkyl), —OC(O)N($C_{1-4}$ alkyl)($C_{1-4}$ alkyl), —NHC(O)($C_{1-4}$ alkyl), —NHC(O)($C_{1-4}$ alkoxy), —N($C_{1-4}$ alkyl) C(O)($C_{1-4}$ alkyl), —N($C_{1-4}$ alkyl)C(O)($C_{1-4}$ alkoxy), —OC(O)($C_{1-4}$ alkyl), —OC(O)($C_{1-4}$ alkoxy), —Si($C_{1-4}$alkyl)$_3$, —Si($C_{1-4}$ alkoxy)$_3$, $C_{6-10}$aryl, $C_{6-10}$aryloxy, $C_{6-10}$arylthio, $C_{6-10}$heteroaryl, —($C_{1-8}$-perhaloalkyl), aryl$C_{2-6}$alkynyl, —$C_{2-6}$alkenyl, heteroaryl$C_{2-6}$alkynyl, —$C_{2-6}$alkenyl, $C_{3-8}$cycloalkyl, —$NR^8R^9$ where $R^8$ and $R^9$ are independently H, —$C_{1-4}$alkyl —$C_{2-4}$alkenyl, —$C_{2-4}$alkynyl or combine with the interjacent nitrogen to form a five- or six-membered ring which may comprise one or two or three heteroatoms (one or two N, O or S atoms in addition to the interjacent nitrogen atom), in which case the heterocyclic ring is unsubstituted or the heterocyclic ring is substituted by one or two oxo substituent, $C_{1-4}$ alkyl groups, —$C_{2-4}$alkenyl or substituted —$C_{2-4}$alkenyl, —$C_{2-4}$alkynyl or substituted —$C_{2-4}$alkynyl, —C(O)H, —C(O)($C_{1-4}$ alkyl), —C(O)($C_{1-4}$alkoxy), —C(O)$NH_2$, —C(O)NH($C_{1-4}$ alkyl), —C(O)N($C_{1-4}$ alkyl)($C_{1-4}$ alkyl), —OC(O)NH($C_{1-4}$ alkyl), —OC(O)N($C_{1-4}$ alkyl) ($C_{1-4}$ alkyl), —NHC(O)($C_{1-4}$ alkyl), —NHC(O)($C_{1-4}$ alkoxy), —N($C_{1-4}$ alkyl)C(O)($C_{1-4}$ alkyl), —N($C_{1-4}$ alkyl) C(O)($C_{1-4}$ alkoxy), —OC(O)($C_{1-4}$ alkyl), —OC(O)($C_{1-4}$ alkoxy), —Si($C_{1-4}$ alkyl)$_3$, —Si($C_{1-4}$ alkoxy)$_3$, $C_{6-10}$aryl, $C_{6-10}$aryloxy, $C_{6-10}$arylthio, $C_{6-10}$heteroaryl, —($C_{1-8}$-perhaloalkyl), aryl$C_{1-4}$-alkynyl, —$C_{1-6}$alkynyl, wherein all the alkyl, alkenyl, alkynyl, alkoxy, aryl, aryloxy, arylthio or heteroaryl groups are either substituted or unsubstituted, preferably these substituents of the substituted groups bear only one further substituent, more preferably these substituents of the substituted groups are not further substituted.

The more preferred substituents of the substituted alkyl groups, alkenyl groups, the alkynyl groups and the alkoxy are selected from the following substituents —OH, CN, F, Cl, $C_{1-4}$alkoxy, —$C_{1-4}$alkoxy, —$C_{1-4}$ alkylthio, $C_{1-4}$alkyl, $C_{2-4}$alkenyl, $C_{2-4}$alkenyl, $C_{2-4}$alkinyl, $C_{6-10}$aryl, —$C_{1-4}$alkylamino. The alkyl groups are branched or linear. The most preferred alkyl groups are methyl, ethyl, propyl, iso-propyl, n-butyl, t-butyl (1,1-diemthylethyl), sec-butyl (1-methylpropyl), iso-butyl (2-methylpropyl), pentyl, iso-pentyl (3-methylbutyl, isoamyl), 1-methylpentyl, 1-ethylpentyl, hexyl, heptyl, or octyl. Preferred alkenyl groups are ethenyl, propenyl (1-propenyl, 2-propenyl), butenyl (1-butenyl, 2-butenyl, 3-butenyl, 2-methylpropen-1-yl, 2-methylpropen-2-yl), pentenyl (pent-1-enyl, pent-2-enyl, pent-3-enyl, 2-methylbut-1-enyl, 3-methylbut-1-enyl, 2-methylbut-2-enyl, 3-methylbut-2-enyl, 2-methylbut-3-enyl, 3-methylbut-3-enyl, 1,2-dimethylprop-2-enyl, 1,1-dimethylprop-2-enyl). Preferred alkynyl groups are ethinyl, propinyl (prop-1-inyl or prop-2-inyl (propargyl)), butyl (but-1-ynyl, but-2-ynyl, but-3-ynyl), pentinyl (pent-1-inyl, pent-2-inyl, pent-3-inyl, pent-4-yl, 3-methylbut-1-inyl, 2-methylbut-3-inyl, 1-methylbut-3-inyl). The most preferred alkyl groups and the most preferred alkoxy groups are methyl, ethyl, propyl, t-buyl, methoxy and ethoxy groups. Methyl, ethyl and methoxy groups are very particularly preferred.

Preferably the alkyl groups in the compound of formula (I) and/or the alkoxy groups in the compound of formula (I) bear not more than two further substituents, more preferably the alkyl groups in the compound of formula (I) and/or the alkoxy groups in the compound of formula (I) bear not more than one further substituent, most preferred the alkyl groups in the compound of formula (I) and/or the alkoxy groups in the compound of formula (I) are not further substituted.

The more preferred substituents of the substituted aryl groups in the compound of formula (I) are selected from the following substituents F, Cl, $CF_3$, CN, —OH, nitro, —$C_{1-4}$ alkyl, —$C_{1-4}$ alkoxy, —C(O)($C_{1-4}$ alkoxy), —C(O)H, —C(O)($C_{1-4}$ Alkyl) wherein the alkyl groups are either substituted or unsubstituted. The aryl groups are preferably naphthyl, phenantrenyl or phenyl groups, more preferably phenyl groups.

The most preferred substituents of the substituted aryl groups in the compound of formula (I) are selected from the following substituents, F, Cl, —$C_{1-4}$Alkyl, $C_{1-4}$alkoxy, —CN, —C(O)($C_{1-4}$ alkoxy), —C(O)($C_{1-4}$ Alkyl) and preferably F, Cl are the even more preferred substituents of the substituted aryl groups in the compound of formula (I).

In particularly preferred embodiments of the invention, the preferred groups for A, D, X, R, $R^1$, $R^2$, $R^3$, $R^4$, $R^5$ and $R^6$ in any combination thereof, are as set out below.

When A and/or D is alkyl, it may be linear or branched and is preferably $C_{1-12}$-, more preferably $C_{1-8}$- and especially $C_{1-4}$-alkyl.

When A and/or D is substituted alkyl, the substituent may be $C_{1-6}$-alkoxy, hydroxy, halogen, nitrile, amino, substituted amino, carboxy, acyl, aryloxy or carbonylamino optionally substituted by $C_{1-6}$-alkyl.

When A and/or D is alkyl the alkyl group or groups are preferably unsubstituted.

When A and/or D is aryl, it is preferably phenyl which may itself be substituted.

When A and/or D is arylalkyl, it is preferably benzyl or 2-ethylphenyl, where the phenyl ring may be substituted.

When the phenyl ring is substituted, the substituents include $C_{1-6}$-alkyl, $C_{1-6}$-alkoxy, aryloxy, hydroxy, halogen, nitro, carbonamido, sulphonamido, trifluoromethyl or amino optionally substituted by one or more $C_{1-6}$-alkyl groups.

Aryloxy is preferably phenoxy.

When A and D together with the two carbon atoms to which they are attached form a fused ring the ring may be alicyclic as in cyclopentene, cyclohexene or cycloheptene or it may be aromatic such as phenyl, pyridyl, thienyl or furanyl. The fused ring may also contain more than one ring system, for example, a naphthyl or quinolinyl ring system or the fused ring may also link two oxaborole rings as for example in 1H,3H-benzo[1,2-c: 4,5-c']bis[1,2]oxaborole.

When $R^1$ and/or $R^2$ is aryl it is preferably phenyl.

When $R^1$ and/or $R^2$ is alkyl it is preferably methyl

When $R^1$ and/or $R^2$ is arylalkyl it is preferably benzyl.

Preferably, at least one of $R^1$ and $R^2$ is hydrogen and it is especially preferred that both are hydrogen.

When R is alkyl it may be linear or branched and is preferably $C_{1-12}$- and especially $C_{1-6}$-alkyl.

When R is substituted alkyl, the substitutent may be $C_{1-6}$-alkoxy, $C_{1-6}$-alkylthio, hydroxy, amino, substituted amino, carboxy, aryl, aryloxy, carbonamido optionally substituted by $C_{1-6}$-alkyl, aryl such as phenyl and aralkyl such as benzyl.

When R is arylalkyl it is preferably benzyl or 2-phenyl-ethyl.

When R is aryl it is preferably phenyl.

When R is heteroaryl it is preferably quinolinyl and particularly quinolin-8-yl.

When R is cycloalkyl it is preferably cyclohexyl or cyclopentyl.

When the substituent is halogen, it is preferably bromine, chlorine and especially fluorine.

One preferred class of oxaborole is a benzoxaborole of formula 1 wherein A and D together with the carbon atoms to which they are attached form a fused phenyl, naphthyl or thienyl ring.

When the fused ring is phenyl, the oxaborole is a benzoxaborole and the substituent or substituents may be in any of positions 4, 5, 6 or 7 of the benzoxaborole. Preferably the substituent or substituents is/are in the 5 and/or 6 position. Preferred substituents are amino, alkyl, alkoxy, phenyl, phenoxy, sulphonamide, carbonamide, each of which may be substituted, and also trifluoromethyl, chlorine, bromine and especially fluorine.

When the fused ring is naphthyl, the other fused phenyl ring is attached to the benzoxaborole ring system in either the 4,5- or 5,6-position.

In one preferred class of oxaborole, R is hydrogen.

In a preferred embodiment according to the present invention there is provided a method for controlling or preventing infestation of plants or plant propagation material and/or harvested food crops susceptible to microbial attack by treating plants or plant propagation material and/or harvested food crops with an effective amount of an oxaborole of general formula (I)

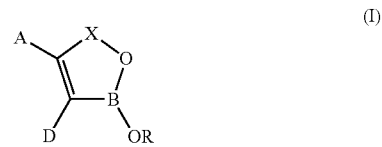

or a salt thereof wherein

A and D, together with the carbon atoms to which they are attached, form a 5, 6 or 7-membered fused ring which may be substituted by $C_{1-6}$-alkyl, $C_{1-6}$-alkoxy, hydroxy, halogen, nitro, nitrile, amino (optionally substituted by one or more $C_{1-6}$-alkyl groups), carboxy, acyl, aryloxy, carbonamido (optionally substituted by $C_{1-6}$-alkyl), sulphonamido or trifluoromethyl or the fused ring may link two oxaborole rings;

X is a group —$CR^1R^2$ wherein $R^1$ and $R^2$ are each, independently, hydrogen, optionally substituted $C_{1-6}$-alkyl, nitrile, nitro, aryl, aralkyl or $R^1$ and $R^2$ together with the carbon atom to which they are attached form an alicyclic ring;

R is hydrogen, $C_{1-18}$-alkyl (optionally substituted by $C_{1-6}$-alkoxy, $C_{1-6}$-alkylthio, hydroxy, amino (optionally substituted by $C_{1-18}$-alkyl), carboxy, aryl, aryloxy, carbonamido (optionally substituted by $C_{1-6}$-alkyl, aryl, arylalkyl, aralkyl, aryl, heteroaryl, cycloalkyl, $C_{1-18}$-alkyleneamino (optionally substituted by phenyl, $C_{1-6}$-alkoxy, $C_{1-6}$-alkylthio or a oxo substituent), carbonylalkyleneamino or a radical of formula (II):

wherein A, D and X are as defined above.

Another preferred class of oxaboroles for use in the present invention is where R is substituted alkyl, especially where the substituent is a primary, secondary or tertiary amino group and particularly wherein the alkylene amino group forms a 5-, 6- or 7-membered ring together with the boron atom and the oxygen atom to which the group R is attached. Such compounds are esters as for example in formula (2) below

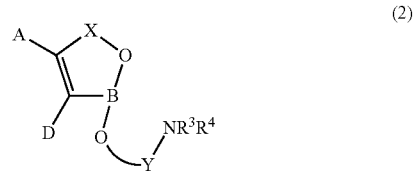

wherein

A, D and X are as defined hereinbefore; $R^3$ and $R^4$ are each independently, hydrogen, optionally substituted $C_{1-18}$-alkyl or optionally substituted phenyl or $R^3$ together with Y or part of Y forms a 5- or 6- or 7-membered optionally substituted ring containing the nitrogen atom; and Y is an optionally substituted divalent alkylene linking group containing up to 18 carbon atoms preferably up to 6 carbon atoms. $R^3$ and $R^4$ are preferably optionally substituted $C_{1-12}$-alkyl, more preferably optionally substituted $C_{1-8}$-alkyl and especially substituted $C_{1-6}$-alkyl.

Another preferred class of oxaboroles for use in the present invention is where R is substituted alkyl, especially where the substituent is a primary, secondary or tertiary amino group and particularly wherein the alkylene amino group forms a 5-, 6- or 7-membered ring together with the boron atom and the oxygen atom to which the group R is attached. Such compounds are esters containing a tetrahedral boron atom as for example in formula (3) below

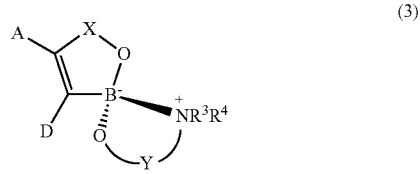

(3)

wherein
A, D and X are as defined hereinbefore; $R^3$ and are each independently, hydrogen, optionally substituted $C_{1-18}$-alkyl or optionally substituted phenyl or $R^3$ together with Y or part of Y forms a 5- or 6- or 7-membered optionally substituted ring containing the nitrogen atom; and Y is an optionally substituted divalent alkylene linking group containing up to 18 carbon atoms preferably up to 6 carbon atoms. $R^3$ and are preferably optionally substituted $C_{1-12}$ alkyl, more preferably optionally substituted $C_{1-8}$-alkyl and especially substituted $C_{1-6}$ alkyl.

Preferably A, D and X are as defined hereinbefore; $R^3$ and $R^4$ are each independently, hydrogen, optionally substituted $C_{1-18}$-alkyl or optionally substituted phenyl and Y is an optionally substituted divalent alkylene linking group containing up to 18 carbon atoms preferably up to 6 carbon atoms. $R^3$ and $R^4$ are preferably optionally substituted $C_{1-12}$-alkyl, more preferably optionally substituted $C_{1-8}$-alkyl and especially substituted $C_{1-6}$-alkyl.

It is preferred that when $R^3$ and/or $R^4$ is alkyl the alkyl group is unsubstituted.

The alkylene group represented by Y may be linear or branched.

When Y is substituted alkylene the substituent is preferably phenyl, $C_{1-6}$-alkyl, $C_{1-6}$-alkoxy, $C_{1-6}$-alkylthio or carbonyl alkylene as for example a —COCH$_2$— group, more preferably, $C_{1-6}$-alkyl.

When Y or part of Y forms a 5-, 6- or 7-membered optionally substituted ring the substituent may be a fused ring which may itself be substituted.

Preferably Y is unsubstituted $C_{1-6}$-alkylene or substituted $C_{1-6}$-alkylene.

When $R^3$ together with Y forms a 6-membered optionally substituted ring the ring is preferably a quinolinyl ring as obtainable, for example, from 8-hydroxyquinoline.

When $R^3$ together with part of Y forms a 5-membered ring the ring is preferably pyrrolidin-2-yl.

It is preferred that A and D together with the carbon atoms to which they are attached form an aromatic ring or ring system such as for example a fused phenyl, thienyl or naphthyl ring which ring or ring system may be substituted as defined hereinbefore for substituted phenyl and substituted alkyl. Preferably A and D together with the carbon atoms to which they are attached form an substituted fused phenyl ring optionally substituted by chlorine, fluorine, nitro, phenoxy or trifluoromethyl.

Preferably A and D together with the carbon atoms to which they are attached form an substituted fused phenyl ring optionally substituted by chlorine, fluorine, nitro, phenoxy or trifluoromethyl.

More preferably A and D together with the carbon atoms to which they are attached form an optionally substituted fused phenyl ring optionally substituted by chlorine, fluorine, nitro, phenoxy or trifluoromethyl.

When A and D together with the carbon atoms to which they are attached form a fused phenyl ring which is substituted, the oxaborole may be a 1H,3H-benzo[1,2-c:4,5c']bis[1,2]oxaborole containing an ester group attached to each boron atom.

A particularly preferred class of oxaborole of formula 3 is that of formula (4)

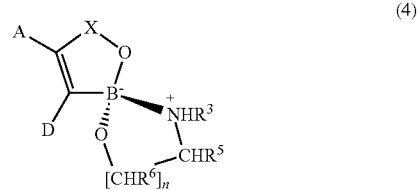

(4)

wherein:
A, D and X are as defined hereinbefore; n is 1, 2 or 3; $R^3$ is hydrogen, optionally substituted $C_{1-18}$-alkyl or optionally substituted phenyl; $R^5$ and $R^6$ are each independently, hydrogen, optionally substituted alkyl containing up to a total of 16 carbon atoms or optionally substituted phenyl.

Preferably $R^5$ and $R^6$ are each, independently, optionally substituted $C_{1-6}$- and especially optionally substituted $C_{1-4}$-alkyl.

Preferably two of $R^3$, $R^5$ and $R^6$ are hydrogen. It is especially preferred that $R^3$ and $R^5$ are both hydrogen.

Preferably n is 1 or 2. In a further preferred embodiment n is 1; In an other further preferred embodiment n is 1.

When A and/or D and/or R is a group which is or contains halogen the halogen may be fluorine, chlorine, bromine or iodine. When A and/or D is alkyl substituted by halogen, it may contain more than one halogen atom as in trifluoromethyl.

Any substituent in the fused ring form by A and D with the two carbon atoms to which they are attached is preferably attached to a carbon atom other than that adjacent to the oxaborole ring. Thus in the case of 1,2-dihydro-2,1-benzoxaboroles the substituent or substituents are preferably in the 5 and/or 6 position.

When the oxaborole of formula I is a salt, the group —OR attached to the boron atom is ionic as in —O—R$^+$ where R$^+$ is an alkali metal such as lithium, potassium or sodium or R$^+$ is an amine or quaternary ammonium cation. In the latter case the quaternary ammonium ion may itself be microbiologically active.

When A and/or D and/or R contains amino or substituted amino the salt of the oxaborole of formula I may be the salt of an organic or inorganic acid. Examples of such acids are acetic and hydrochloric acids.

Particularly useful effects have been obtained where the compound containing an oxaborole ring is benzoxaborole or the 6-chloro-, 5-chloro-, 5-fluoro- or 5-bromo-derivative thereof and the oxaborole esters obtainable therefrom by reaction with alkanoamines such as ethanolamine, 3-amino-propanol, 2-aminobutanol and 4-aminobutanol.

A particularly preferred class of oxaborole of formula (I) is that of formula (Ia)

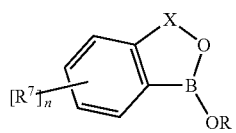

(Ia)

wherein all the substituents are as defined above and $R^7$ is $C_{1-6}$-alkyl, $C_{1-6}$-alkoxy, hydroxy, halogen, nitro, nitrile, amino (optionally substituted by one or more $C_{1-6}$-alkyl groups), carboxy, acyl, aryloxy, carbonamido (optionally substituted by $C_{1-6}$-alkyl), sulphonamido or trifluoromethyl and n is 0, 1, 2, 3; preferably $R^7$ is chlorine, fluorine, nitro, phenoxy and n is 0 or 1.

A particularly preferred class of oxaborole of formula (I) is that of formula (Ib)

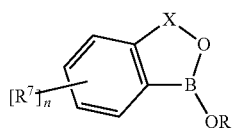

(Ib)

wherein $R^7$ is $C_{1-6}$-alkyl, $C_{1-6}$-alkoxy, hydroxy, halogen, nitro, nitrile, amino optionally substituted by one or more $C_{1-6}$-alkyl groups, carboxy, acyl, aryloxy, carbonamido optionally substituted by $C_{1-6}$-alkyl, sulphonamido or trifluoromethyl; n is 0, 1, 2, 3; X is $CH_2$; and R is H, $C_{1-6}$ alkyl optionally substituted by —$NR^3R^4$ wherein $R^3$ and $R^4$ are each independently, hydrogen, optionally substituted $C_{1-4}$-alkyl.

Preferably $R^7$ is chlorine, fluorine, nitro, phenoxy; X is $CH_2$ and R is H, $C_{1-4}$ alkyl optionally substituted by —$NR^3R^4$ wherein $R^3$ and $R^4$ are each independently, hydrogen, optionally substituted $C_{1-4}$-alkyl and n is 0 or 1.

More preferably $R^7$ is chlorine, fluorine, X is $CH_2$ and R is H, $C_{1-4}$ alkyl optionally substituted by —$NR^3R^4$ wherein $R^3$ and $R^4$ are each independently, hydrogen, optionally substituted $C_{1-4}$-alkyl and n is 0 or 1.

A particularly preferred class of oxaborole of formula (I) is that of formula (Ic)

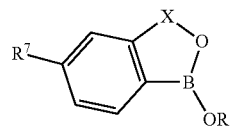

(Ic)

wherein $R^7$ is $C_{1-6}$-alkyl, $C_{1-6}$-alkoxy, hydroxy, halogen, nitro, nitrile, amino optionally substituted by one or more $C_{1-6}$-alkyl groups, carboxy, acyl, aryloxy, carbonamido optionally substituted by $C_{1-6}$-alkyl, sulphonamido or trifluoromethyl; X is $CH_2$; and R is H, $C_{1-6}$ alkyl optionally substituted by —$NR^3R^4$ wherein $R^3$ and $R^4$ are each independently substituted $C_{1-4}$-alkyl;

Preferably $R^7$ is chlorine, fluorine, nitro, phenoxy; X is $CH_2$ and R is H, $C_{1-4}$ alkyl optionally substituted by —$NR^3R^4$ wherein $R^3$ and $R^4$ are each independently, hydrogen, optionally substituted $C_{1-4}$-alkyl;

More preferably $R^7$ is chlorine, fluorine, X is $CH_2$ and R is H, $C_{1-4}$ alkyl optionally substituted by —$NR^3R^4$ wherein $R^3$ and $R^4$ are each independently, hydrogen, optionally substituted $C_{1-4}$-alkyl.

In one preferred embodiment more preferably $R^7$ is chlorine, X is $CH_2$ and R is H, $C_{1-4}$ alkyl optionally substituted by —$NR^3R^4$ wherein $R^3$ and $R^4$ are each independently, hydrogen, optionally substituted $C_{1-4}$-alkyl.

In a further preferred embodiment more preferably $R^7$ is fluorine, X is $CH_2$ and R is H, $C_{1-4}$ alkyl optionally substituted by —$NR^3R^4$ wherein $R^3$ and $R^4$ are each independently, hydrogen, optionally substituted $C_{1-4}$-alkyl Methods for the preparation of compounds of formula (I) comprise the following schemes, wherein the substituents have the meaning as described above.

Compounds of formula (I) with for example X=$CH_2$ may be prepared by reacting compounds of type A, where Y can be hydrogen or a suitable protecting group, such as methylmethoxy and Q can be hydrogen or a halogen such as bromine or iodine, with organometallic reagents such as butyllithium, sec-butyllithium or isopropylmagnesium chloride in an appropriate solvent such as tetrahydrofuran at a temperature between −75° C. and 25° C. The organometallic intermediate can be quenched with a boronic ester to obtain compounds B, where R can be hydrogen or alkyl and cycloalkyl group. Treatment of compounds of type B with an acid such as hydrochloric acid gives compounds of formula (Ia). Compounds of formula (I) can be obtained reacting compounds of type (Ia) with the appropriate alcohol, in particular an aminoalcohol or an amino acid, in a solvent such as toluene at a temperature between 25° C. and 100° C.

Procedures for the preparation of compounds of type (Ia) and (I) can be found in WO9533754; US070155699; WO07078340; Tetrahedron Letters, 2010, 51, 4482-4485; Med. Chem. Lett., 2010, 1, 165-169; Tetrahedron, 2007, 63, 9401-9405.

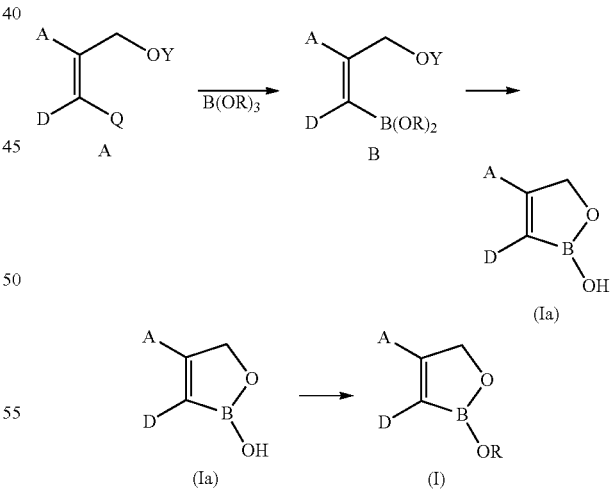

The invention therefore also relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

An improvement in the growing (or growth) characteristics of a plant can manifest in a number of different ways, but ultimately it results in a better product of the plant. It can, for example, manifest in improving the yield and/or vigour of the plant or quality of the harvested product from the plant.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed in terms of an amount by weight or volume of a product of the plant on a specific basis. Said basis can be expressed in terms of time, growing area, weight of plants produced, amount of a raw material used, or the like.

As used herein the phrase "improving the vigour" of a plant relates to an increase or improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that a method is capable of "improving the yield and/or vigour" of a plant, the present method results in an increase in either the yield, as described above, or the vigor of the plant, as described above, or both the yield and the vigor of the plant.

A compound of formula I can also be used to treat stored products, such as grain, for protection against pyhtopathogenic diseases.

The methods according to the instant invention are particularly effective to protect useful plants or plant propagation material thereof against phytopathogenic fungi belonging to the following classes: Ascomycetes (e.g. the genus *Cochliobolus, Colletotrichum, Fusarium, Gaeumannomyces, Pythium, Giberella, Monographella, Microdochium, Penicillium, Phoma, Pyricularia, Magnaporthe, Septoria, Pseudocercosporella, Tapesia* and *Thielaviopsis*); Basidiomycetes (e.g. the genus *Phakopsora, Puccinia, Rhizoctonia, Thanatephorus, Sphacelotheca, Tilletia, Typhula* and *Ustilago*); Fungi imperfecti (also known as Deuteromycetes; e.g. the genus *Ascochyta, Diplodia, Erysiphe, Fusarium,* *Helminthosporium, Phomopsis, Pyrenophora* and *Verticillium*); Oomycetes (e.g. *Aphanomyces, Peronospora, Peronosclerospora, Phytophthora, Pseudoperonospora, Pythium*); and Zygomycets (e.g. the genus *Rhizopus*); especially against *Aphanomyces* spp., *Pythium* spp, *Giberella*-. and *Fusarium* spp.

Within the scope of the invention, useful plants to be protected typically comprise the following species of plants: cereal (wheat, barley, rye, oat, rice, maize, sorghum and related species); beet (sugar beet and fodder beet); pomes, grapes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucum-bers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as turf and ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" "useful crops" are to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" or "useful crops" are to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "crops" or the term "useful plants" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*. In a preferred embodiment the plants mentioned in this application are living plants, more preferably still growing plants.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing or a seed grow medium or plant grow medium.

Seed grow medium or plant grow medium according to the present application are manmade (organic or inorganic) as well as organic natural mediums. These mediums include Oasis® cubes, expanded clay pellets, rockwool, coconut fiber, sand, gravel, perlite, sphagnum moss, water, vermiculite, fiberglass insulation, saw dust, soilless mixes (which comprise at least one component selected from spaghnam moss, perlite and vermiculite and retain water well and have great wicking action while still holding a good amount of air), air, lava rock, and natural soil but preferable the seed growing or plant growing medium are selected from Oasis® cubes, expanded clay pellets, rockwool, coconut fiber, sand, gravel, perlite, sphagnum moss, water, vermiculite, fiberglass insulation, saw dust, soilless mixes, lava rock.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds. A seed is a small embryonic plant enclosed in a covering called the seed coat, usually with some stored food. Seeds are living organisms in a dormant stage. In order to germinate the seed must be viable, that is, the embryo must be alive. In the preferred embodiment the seed of the present application is capable of germination. See for example http://www.tomatosphere.org/teacher-resources/teachers-guide/principal-investigation/seeds-germination.cfm or "Hartmann & Kester's Plant Propagation: Principles and Practices"; Hudson T. Hartmann (Author), Dale E. Kester (Author), Fred T. Davies (Author), Robert Geneve (Author); Prentice Hall; 8th edition (Oct. 31, 2010); ISBN-10: 0135014492 or ISBN-13: 978-0135014493 chapter 7 page 200 or "Botanik" Ulrich Lunge (Autor), Manfred Kluge (Autor) Gabriela Bauer (Autor); Verlag: Wiley-VCH; 4. Verbesserte Auflage, veränderte Auflage (2002) ISBN-10: 3-527-30623-4, page 549 left column or "Lehrbuch der Botanik für Hochschulen" begründet von E. Strasburger, F. Noll, H. Schenk, A. F. W. Schimper neubearbeitet von von Peter Sitte, Hubert Ziegler, Friedrich Ehrendorfer and Andreas Bresinsky (1991) 33. Neubearbeitete Auflage Gustav Fischer Verlag, Stuttgart, Jena, New York ISBN 3-437-20447-5 see page page 708, left column third paragraph. Likewise the same is the case for tubers (stem tubers and root tubers) which are alive but dormant.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants (auxiliaries) can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I may be applied before or after infection of the plant propagation material by the fungi.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant or, if desired as well, a further, other biocidally active ingredient, is prepared in a known manner, typically by intimately mixing and/or grinding the compound with extenders, for example solvents, solid carriers and, optionally, surface-active compounds (surfactants).

The present invention relates additionally to mixtures comprising at least a compound of formula I and at least a further, other biocidally active ingredient and optionally further ingredients. The further, other biocidally active ingredient are known for example from "The Pesticide Manual" [The Pesticide Manual—A World Compendium; Thirteenth Edition (New edition (2 Nov. 2003)); Editor: C. D. S. Tomlin; The British Crop Protection Council, ISBN-10: 1901396134; ISBN-13: 978-1901396133] or its electronic version "e-Pesticide Manual V4.2" or from the website http://www.alanwood.net/pesticides/ or preferably one of the further pesticides listed below.

Some compositions according to the invention have a systemic action and can be used as foliar, soil and seed treatment fungicides.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed dressing agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Alternatively or in addition one or more materials may be applied on a suitable substrate, for example a seed which is not intended for germination but which is sown together with the plant propagation material and therefore controlling or preventing pest damage in the growing plant which grows from the plant propagation material.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications).

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the pesticide is applied to the soil but would include any application practice that would target the seed during the planting process.

Preferably, the treatment occurs before sowing of the seed so that the sown seed has been pre-treated.

The compounds of formula I are usually applied to the plant propagation material together with adjuvants customary in formulation technology. The compounds of formula I are preferably applied to plant propagation material in the form of compositions, but also can be applied to the plant propagation material simultaneously or in succession, with further compounds. These "further compounds" can be for example fertilizers, micronutrient donors, other preparations that influence plant growth, plant growth regulators, herbicides, insecticides, fungicides, bactericides, insect growth regulators, nematicides or molluscicides or mixtures of several of these preparations, such as two fungicides or a fungicide and an insecticide, if desired together with adjuvants, such as carriers, surfactants or other application-promoting adjuvants customarily employed in the art of formulation.

In a preferred embodiment the invention provides a method of controlling phytopathogenic diseases on useful plants or plant propagation material thereof, which comprises applying to said plant propagation material a fungicidally effective amount of a plant propagation material protecting composition comprising a compound of formula I together with a suitable carrier therefor.

A preferred application method is seed treatment.

Plant propargation material coating or more preferably seed coating, in the broadest sense, includes any process for the addition of materials to the seed; in the simplest form, it is the direct application of a material to seeds. The term "coated plant propargation material" or more preferably the term "coated seed" therefore means, in the broadest sense, a plant propargation material or preferably a seed to which material has been added; in the simplest form, it is the direct application of a material to plant propargation material or seeds. Therefore the material added to the seed comprises the compound according to the formula (I). In the present application a seed comprising a compound according to the formula (I) denotes a seed to which a compound according to the formula (I) has been added which includes that the compound according to the formula (I) is adhering to the surface of the seed. Likewise a plant propargation material comprising a compound according to the formula (I) denotes a plant propargation material to which a compound according to the formula (I) has been added which includes that the compound according to the formula (I) is adhering to the surface of the plant propargation material.

The techniques of seed treatment application are well known to those skilled in the art, and they may be used readily in the context of the present invention see for example Maude, R. B.; Seed treatment Pesticide Outlook (1990), 1, (4), pages 16-22. CODEN:PEOUEN ISSN:0956-1250 or CONCEPTS AND A. G. Taylor and G. E. Harman, TECHNOLOGIES OF SELECTED SEED TREATMENTS, Annu Rev. Phytopathol., 1990, (28) pages 321-339. The compounds of formula I or plant propagation material protecting compositions comprising compounds of formula I together with a suitable carrier therefor can be formulated and applied as a slurry, a solid seed coating, a soak, or as a dust on the surface of the seed. There also may be mentioned, e.g., film-coating or encapsulation. The coating processes are well known in the art, and employ, for seeds, the techniques of film-coating or encapsulation, or for the other multiplication products, the techniques of immersion. Needless to say, the method of application of the compounds of formula I or of compositions comprising compounds of formula I together with a suitable carrier therefor to the seed may be varied and the invention is intended to include any technique which is to be used.

A preferred method of applying compounds of formula I or plant propagation material protecting compositions comprising compounds of formula I together with a suitable carrier therefor consists in spraying or wetting the plant propagation material with a liquid preparation, or mixing the plant material with a solid preparation of the compounds of formula I or plant propagation material protecting compositions comprising compounds of formula I together with a suitable carrier therefor.

The compounds of formula I or plant propagation material protecting compositions comprising compounds of formula I together with a suitable carrier therefor may be formulated or mixed in the seed treater tank or combined on the seed by overcoating with other seed treating agents. The agents to be mixed with the compounds of formula I or plant propagation material protecting compositions comprising compounds of formula I together with a suitable carrier therefor may be for the control of pests, modification of growth, nutrition, or for the control of plant diseases.

The plant propagation material protecting compositions applied to plant propagation material according to the instant invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such plant propagation material protecting compositions may be produced in conventional manner, e.g. by mixing the active ingredients with appropriate formulation inerts (solid or liquid carriers and optionally other formulating ingredients such as surface-active compounds (surfactants), biocides, anti-freezers, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

Such plant propagation material protecting compositions may comprise one or more further pesticides, for example a fungicide, acaricide, bactericide, insecticide, molluscicide, nematicide, rodenticide, two fungicides or a fungicide and an insecticide.

The term "carrier" according to the invention denotes a natural or synthetic, organic or inorganic material with which the compound of formula I is combined in order to facilitate its application to the plant, to the seeds or to the soil. This carrier is hence generally inert, and it must be agriculturally acceptable, in particular to the plant being treated. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

Solid carriers which may be used, for example for dusts and dispersible powders, are calcite, talc, kaolin, montmorillonite or attapulgite, highly-disperse silica or absorptive polymers. Possible particulate, adsorptive carriers for granules are pumice, crushed brick, sepiolite or bentonite, montmorillonite-type clay, and possible nonsorbent carrier materials are calcite or dolomite.

Suitable liquid carriers are: aromatic hydrocarbons, in particular the fractions $C_8$ to $C_{12}$, such as xylene mixtures or substituted naphthalenes, phthalic esters such as dibutyl or dioctyl phthalate, aliphatic hydrocarbons such as cyclohexane or paraffins, alcohols and glycols as well as their ethers and esters, such as ethylene glycol monomethyl ether, ketones such as cyclohexanone, strongly polar solvents such as N-methyl-2-pyrrolidone, dimethyl sulfoxide or dimethylformamide, and, if appropriate, epoxidized vegetable oils or soybean oil; or water.

Suitable surface-active compounds are non-ionic, cationic and/or anionic surfactants having good emulsifying, dispersing and wetting properties, depending on the nature of the active ingredients to be formulated (whether only compounds of formula I or compounds of formula I in combination with other active ingredients). Surfactants will also be understood as meaning mixtures of surface-active compounds.

The surfactants customarily employed in formulation technology are described, inter alia, in the following publications:
"McCutcheon's Detergents and Emulsifiers Annual", MC Publishing Corp., Glen Rock, N.J., 1988.
M. and J. Ash, "Encyclopedia of Surfactants", Vol. I-III, Chemical Publishing Co., New York, 1980-1981.

Among the suitable surfactants there may be mentioned, e.g., polyacrylic acid salts, lignosulphonic acid salts, phenolsulphonic or (mono- or di-alkyl)naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol) phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols. The presence of at least one surfactant is often required because the active ingredients and/or the inert vehicles are not soluble in water and the carrier for the application is water.

Furthermore, particularly useful adjuvants which enhance application are natural or synthetic phospholipids from the series of the cephalins and lecithins, for example phosphatidylethanolamine, phosphatidylserine, phosphatidylglycerine or lysolecithin.

The plant propagation material protecting composition may also comprise at least one polymer from water-soluble and water-dispersible film-forming polymers that improve the adherence of at least the compounds of formula I to the treated plant propagation material, which polymer generally has an average molecular weight of at least 10,000 to about 100,000.

Typically a colouring agent, such as a dye or pigment, is included in the plant propagation material protecting composition, so that an observer can immediately determine that the plant propagation material is treated. Plant propagation material protecting compositions comprising a colouring agent are preferred embodiments of the plant propagation material protecting compositions according to the invention, as they improve user and consumer safety. The colouring agent is also useful to indicate to the user the degree of uniformity of the applied plant propagation material protecting composition.

Generally, the colouring agent tends to have a melting point above 30° C., and therefore, is suspended in the plant propagation material protecting composition of the present invention. The colouring agent can also be a soluble compound.

As examples of colouring agents may be mentioned pigment red 48-2 (CAS-7023-61-2), pigment blue 15 (CAS-147-14-8), pigment green 7 (CAS-1328-53-6), pigment violet 23 (CAS-6358-30-1), pigment red 53-1 (CAS-5160-02-1), pigment red 57-1 (CAS 5281-04-9), pigment red 112 (CAS 6535-46-2) or similar colouring agents.

The plant propagation material protecting compositions tend to comprise between 0.1 to 10% by mass of a colouring agent.

Whereas commercial products will preferably be formulated as concentrates (known as a pre-mix composition (or concentrate, formulated compound (or product)), the end user will normally employ diluted formulations, optionally also containing one or more other pesticide pre-mixes (known as a tank mix composition (or ready-to-apply, spray broth, or slurry)) for treatment of the propagation material, but can also be use appropriately formulated pre-mix compositions.

The tank-mix compositions are generally prepared by diluting with a solvent (for example, water) the one or more pre-mix compositions containing different pesticides, and optionally further auxiliaries. Generally, an aqueous tank-mix is preferred.

Accordingly, examples of plant propagation material compositions of inventions include tank-mix or slurry pesticidal compositions and pre-mix or pesticidal formulations.

In general, the formulations include from 0.01 to 90% by weight of active agent, from 0 to 20% agriculturally acceptable surfactant and 10 to 99.99% solid or liquid carries and adjuvant(s), the active agent consisting of at least the compound of formula I and optionally other active agents, particularly microbiocides or conservatives or the like.

Concentrated forms of compositions (such as pre-mix or pesticidal formulations) generally contain in between about 2 and 80%, preferably between about 5 and 70% by weight of active agent.

Tank-mix or slurry forms of concentrated forms of compositions (diluted formulations) may for example contain from 0.01 to 20% by weight, preferably from 0.01 to 5% by weight of active agent.

The amount of a compound of formula I used on the propagation material varies according type of propagation material (e.g., seed or tuber) and plant (for example, wheat seeds generally have less active ingredients adhered thereto than oil seed rape seeds based on equivalent weight of seeds), and is such that the effective fungicidal amount can be determined by biology trials.

When the compounds of formula I or plant propagation material protecting compositions comprising compounds of formula I together with a suitable carrier therefor are used for treating seed, rates of 0.1 to 5000 g of a compound of formula I per 100 kg of seed, preferably from 1 to 1000 g per 100 kg of seed, most preferably from 1 to 100 g per 100 kg of seed are generally sufficient.

The invention further pertains to a product for use in agriculture or horticulture comprising a capsule comprising a seed treated with the compound according to formula (I). In another embodiment, the product comprises a capsule wherein at least a treated or untreated seed and with the compound according to formula (I) are co-located.

The Examples which follow serve to illustrate the invention, "active ingredient" denoting a compound of formula I.

The following non-limiting examples illustrate the above-described invention in greater detail without limiting it.

EXAMPLES

Example 1: Preparation of 5-chloro-1-hydroxy-3H-2,1-benzoxaborole (1)

Step 1: Preparation of (2-bromo-5-chloro-phenyl)methanol (A)

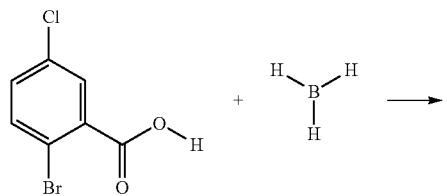

-continued

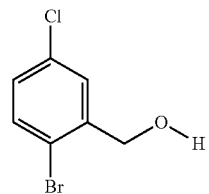

A

A solution of borane-tetrahydrofuran complex in THF (0.15 L, 1.5 eq) was added dropwise to a solution of 2-bromo-5-chlorobenzoic acid (24 g) in anhydrous tetrahydrofuran (0.24 L) at 0° C. and under argon atmosphere. The reaction mixture was stirred at room temperature for 16 h, before being slowly poured onto 0.10 L of a 2N aqueous solution of hydrogen chloride at 0° C. The mixture was stirred for 15 minutes and the volatiles were removed under reduced pressure. The aqueous layer was extracted with ethyl acetate and the combined organic layers were washed with a 1N aqueous solution of sodium hydroxide and then water. After drying over sodium sulfate, filtration and concentration under reduced pressure, the crude product was purified by column chromatography; 23.2 g; M.p. 79-80° C.

Step 2: Preparation of 1-bromo-4-chloro-2-(methoxymethoxymethyl)benzene (B)

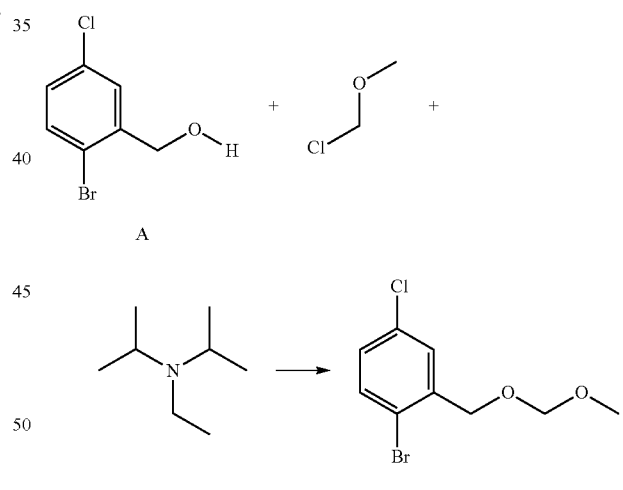

(2-bromo-5-chloro-phenyl)methanol (A, 12 g) was dissolved in dichloromethane (0.35 mL) and cooled to 0° C. Under argon atmosphere, diisopropylethylamine (14 mL, 1.5 eq) and chloromethyl methyl ether (5.0 mL, 1.2 eq) were added. After 1 night of stirring at room temperature, the crude reaction mixture was washed with a saturated solution of sodium hydrogen carbonate, dried over sodium sulfate and evaporated under reduced pressure. Purification by column chromatography afforded 10.5 g of 1-bromo-4-chloro-2-(methoxymethoxymethyl)benzene (B) as an oil.

Step 3: Preparation of 5-chloro-1-hydroxy-3H-2,1-benzoxaborole (1)

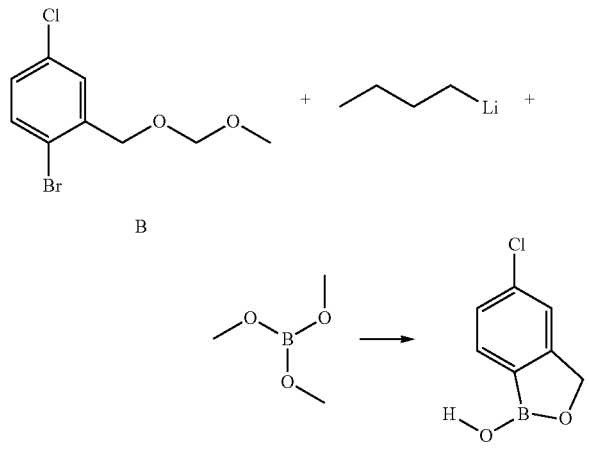

To a solution of (B) (6.0 g) in anhydrous tetrahydrofuran (120 mL) at −78° C. was added dropwise a solution of butyllithium in hexane (15.6 mL, 1.1 eq). To the resulting yellow-brown solution trimethyl borate (2.5 mL, 1.0 eq) was injected in one portion and the cooling bath was removed. The mixture was warmed gradually for 30 minutes. After stirring at room temperature for 2 hours, 8.0 ml of a 6N aqueous solution of hydrogen chloride were added and the reaction mixture was left stirring overnight at room temperature. Evaporation of the volatiles gave a residue which was taken up in ethyl acetate, washed with water, brine, dried over sodium sulfate and then evaporated. The crude product was crystallized from ethyl acetate to give 1.4 g of 5-chloro-1-hydroxy-3H-2,1-benzoxaborole (1) as a white powder. Purification of the filtrate by column chromatography afforded 1.2 g more of 1. M.p. 147-149° C.

Example 2: Preparation of 3-[(5-chloro-3H-2,1-benzoxaborol-1-yl)oxy]propan-1-amine (5)

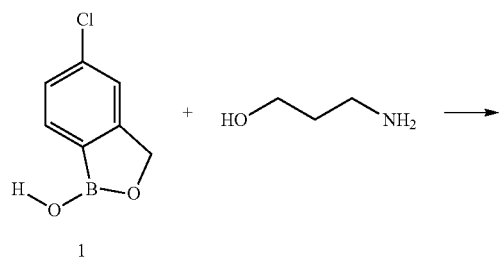

Compound 1 (6.6 g) was dissolved in toluene (0.39 L) at 80° C. and 3-amino-1-propanol (3.0 mL, 1.0 eq) was added. A white precipitate appeared almost immediately and the reaction mixture was allowed to stir for further 5 minutes at 80° C. The mixture was then cooled to room 4° C. with an ice bath. The precipitate formed was filtered, washed with toluene and diethyl ether and dried under vacuum to give 7.9 g of 3-[(5-chloro-3H-2,1-benzoxaborol-1-yl)oxy]propan-1-amine (5). M.p. 203-205° C.

Example 3: Preparation of 1-[(5-chloro-3H-2,1-benzoxaborol-1-yl)oxy]butan-2-amine (2)

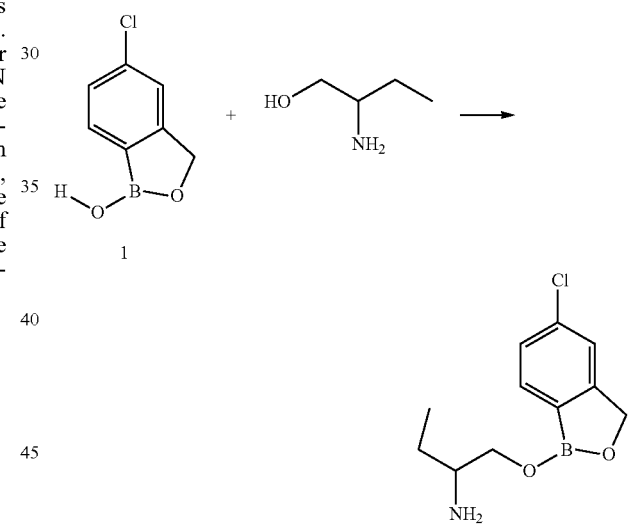

In a similar way as for 5, starting from 10.9 g of 1, 1-[(5-chloro-3H-2,1-benzoxaborol-1-yl)oxy]butan-2-amine (2) was obtained in a 89% yield (13.8 g) as a white powder. M.p. 191-193° C.

TABLE 1

| | Structures 1-36 | |
|---|---|---|
| Compound | Name | Structure |
| 1 | 5-Chloro-3H-benzo[c][1,2]oxaborol-1-ol | |

TABLE 1-continued

Structures 1-36

| Compound | Name | Structure |
|---|---|---|
| 2 | 1-(5-Chloro-3H-benzo[c][1,2]oxaborol-1-yloxymethyl)-propylamine | 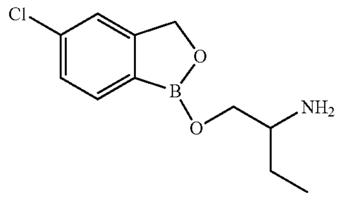 [SMILES: CCC(N)COB1OCc2cc(Cl)ccc21] |
| 3 | 2-(5-Chloro-3H-benzo[c][1,2]oxaborol-1-yloxy)-2-phenyl-ethylamine | 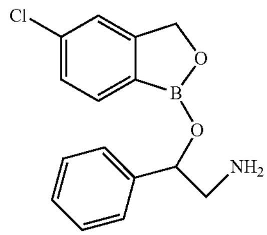 [SMILES: NCC(OB1OCc2cc(Cl)ccc21)c1ccccc1] |
| 4 | [2-(5-Chloro-3H-benzo[c][1,2]oxaborol-1-yloxy)-ethyl]-methyl-amine | 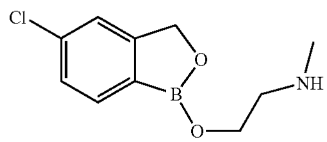 |
| 5 | 3-(5-Chloro-3H-benzo[c][1,2]oxaborol-1-yloxy)-propylamine | 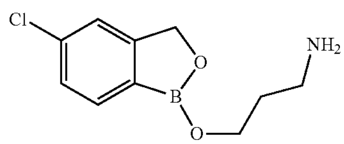 [SMILES: NCCCOB1OCc2cc(Cl)ccc21] |
| 6 | 6-Chloro-3H-benzo[c][1,2]oxaborol-1-ol | 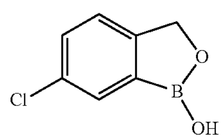 [SMILES: OB1OCc2ccc(Cl)cc21] |
| 7 | 6-Nitro-3H-benzo[c][1,2]oxaborol-1-ol | 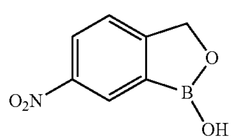 [SMILES: O=[N+]([O-])c1ccc2c(c1)B(O)OC2] |
| 8 | 5-Fluoro-3H-benzo[c][1,2]oxaborol-1-ol | 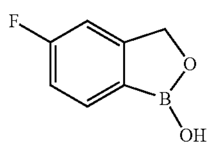 [SMILES: OB1OCc2cc(F)ccc21] |
| 9 | Amino-acetic acid 5-chloro-3H-benzo[c][1,2]oxaborol-1-yl ester | 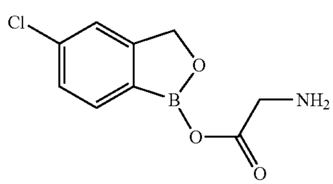 [SMILES: NCC(=O)OB1OCc2cc(Cl)ccc21] |
| 10 | 4-(5-Chloro-3H-benzo[c][1,2]oxaborol-1-yloxy)-butylamine | 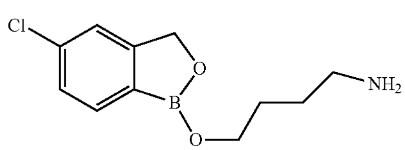 [SMILES: NCCCCOB1OCc2cc(Cl)ccc21] |

TABLE 1-continued

Structures 1-36

| Compound | Name | Structure |
|---|---|---|
| 11 | 3H-Benzo[c][1,2]oxaborol-1-ol | 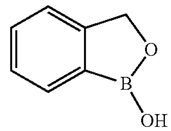 |
| 12 | 3-(5-Fluoro-3H-benzo[c][1,2]oxaborol-1-yloxy)-propylamine | 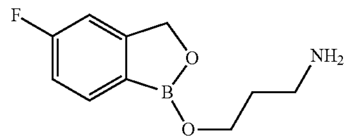 [SMILES: NCCCOB1OCc2cc(F)ccc21] |
| 13 | 4-(5-Fluoro-3H-benzo[c][1,2]oxaborol-1-yloxy)-butylamine | 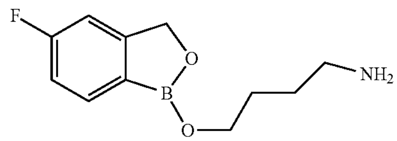 [SMILES: NCCCCOB1OCc2cc(F)ccc21] |
| 14 | 5-Phenoxy-3H-benzo[c][1,2]oxaborol-1-ol | 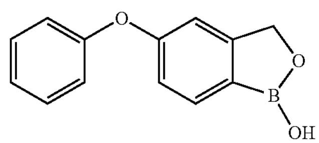 [SMILES: OB1OCc2cc(Oc3ccccc3)ccc21] |
| 15 | 3H-2-Oxa-1-bora-cyclopenta[b]naphthalen-1-ol | 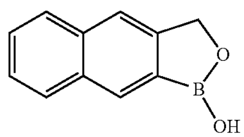 [SMILES: OB1OCc2cc3ccccc3cc21] |
| 16 | 1H-2-Oxa-3-bora-cyclopenta[a]naphthalen-3-ol | 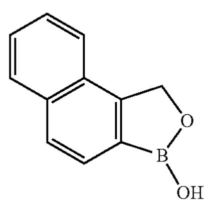 [SMILES: OB1OCc2c1ccc1ccccc21] |
| 17 | 2-(3H-2-Oxa-1-bora-cyclopenta[b]naphthalen-1-yloxy)-ethylamine | 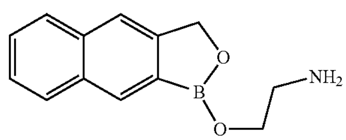 [SMILES: NCCOB1OCc2cc3ccccc3cc21] |
| 18 | 2-(1H-2-Oxa-3-bora-cyclopenta[a]naphthalen-3-yloxy)-ethylamine | 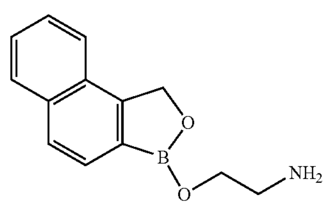 [SMILES: NCCOB1OCc2c1ccc1ccccc21] |
| 19 | 3-Phenyl-3H-benzo[c][1,2]oxaborol-1-ol | 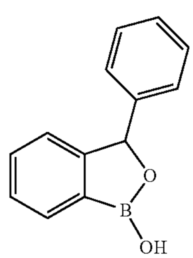 [SMILES: OB1OC(c2ccccc2)c2ccccc21] |

TABLE 1-continued

Structures 1-36

| Compound | Name |
|---|---|
| 20 | (S)-1-Benzyl-2-(5-chloro-3H-benzo[c][1,2]oxaborol-1-yloxy)-ethylamine |
| 21 | 2-(5-Chloro-3H-benzo[c][1,2]oxaborol-1-yloxy)-1,1-dimethyl-ethylamine |
| 22 | 8-(5-Chloro-3H-benzo[c][1,2]oxaborol-1-yloxy)-quinoline |
| 23 | (R)-2-(5-Chloro-3H-benzo[c][1,2]oxaborol-1-yloxy)-1-phenyl-ethylamine |
| 24 | (S)-2-(5-Chloro-3H-benzo[c][1,2]oxaborol-1-yloxymethyl)-pyrrolidine |
| 25 | (S)-2-(5-Chloro-3H-benzo[c][1,2]oxaborol-1-yloxy)-1-phenyl-ethylamine |
| 26 | 2-(5-Chloro-3H-benzo[c][1,2]oxaborol-1-yloxy)-butylamine |
| 27 | 2-(5-Chloro-3H-benzo[c][1,2]oxaborol-1-yloxy)-propylamine |

TABLE 1-continued

Structures 1-36

| Compound | Name | Structure |
|---|---|---|
| 28 | 2-(5-Chloro-3H-benzo[c][1,2]oxaborol-1-yloxy)-1-methyl-ethylamine | 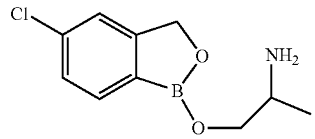 |
| 30 | 1-(5-Fluoro-3H-benzo[c][1,2]oxaborol-1-yloxymethyl)-propylamine | 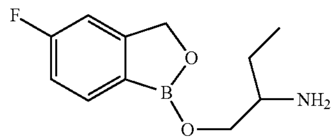 [SMILES: CCC(N)COB1OCc2cc(F)ccc21] |
| 31 | 8-(3H-Benzo[c][1,2]oxaborol-1-yloxy)-quinoline | 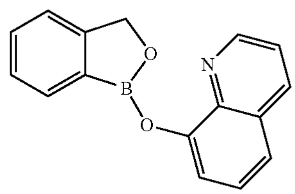 [SMILES: c1ccc2c(c1)COB2Oc1cccc2cccnc12] |
| 32 | 2-(3H-Benzo[c][1,2]oxaborol-1-yloxy)-1,1-dimethyl-ethylamine | 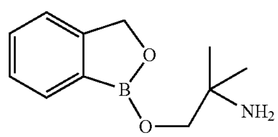 |
| 33 | 2-(5-tert-Butyl-3H-benzo[c][1,2]oxaborol-1-yloxy)-ethylamine | 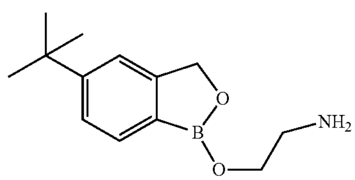 [SMILES: CC(C)(C)c1ccc2c(c1)COB2OCCN] |
| 34 | 5-tert-Butyl-3H-benzo[c][1,2]oxaborol-1-ol | 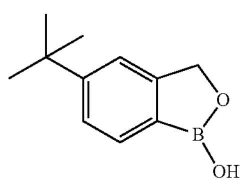 |
| 35 | 2-(5-Phenoxy-3H-benzo[c][1,2]oxaborol-1-yloxy)-ethylamine | 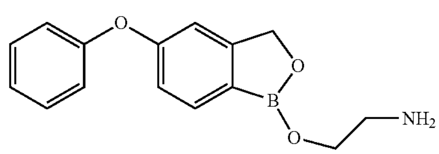 [SMILES: NCCOB1OCc2cc(Oc3ccccc3)ccc21] |
| 36 | 2-(5-Chloro-3H-benzo[c][1,2]oxaborol-1-yloxy)-ethylamine | 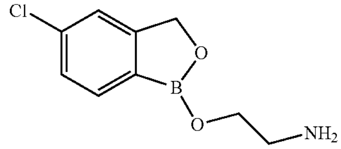 [SMILES: NCCOB1OCc2cc(Cl)ccc21] |

FORMULATION EXAMPLES

| Wettable powders | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |

-continued

| Wettable powders | a) | b) | c) |
|---|---|---|---|
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the finely ground active ingredient is mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the inventive compound/combination. The medium capsule diameter is 8-15 microns. The resulting formulation is applied to seeds as an aqueous suspension in a suitable apparatus.

The following examples illustrate the fungicidal activity of the compounds described in Table 1.

Description of the Methods

*Botryotinia fuckeliana* (*Botrytis cinerea*)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds give at least 80% control on *Botryotinia fuckeliana* at 200 ppm: 1, 2, 3, 4, 5, 6, 8, 9, 10, 11, 12, 13, 15, 16, 20, 21, 22, 23, 24, 25, 26, 27, 28, 30, 31, 32, 36.

*Blumeria graminis* (*Erysiphe graminis*)

Wheat leaf segments cv. Kanzler are placed on agar in a multiwell plate (24-well format) and sprayed with the formulated test compound diluted in water. The leaf disks are inoculated by shaking powdery mildew infected plants above the test plates 1 day after application. The inoculated leaf disks are incubated at 20° C. and 60% rh under a light regime of 24 h darkness followed by 12 h light/12 h darkness in a climate chamber and the activity of a compound is assessed as percent disease control compared to untreated when an appropriate level of disease damage appears on untreated check leaf segments (6-8 days after application). The following compounds give at least 80% control on *Blumeria graminis* at 200 ppm: 8, 14, 35.

*Monographella nivalis* (*Microdochium nivale*)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds give at least 80% control on *Monographella nivalis* at 200 ppm: 1, 2, 3, 4, 5, 6, 7, 8, 9, 10, 12, 13, 14, 15, 16, 18, 19, 20, 21, 22, 23, 24, 25, 26, 27, 28, 30, 31, 32, 34, 35, 36.

*Thanatephorus cucumeris* (*Rhizoctonia solani*)

Mycelia fragments of a newly grown liquid culture of the fungus are directly mixed into nutrient broth (PDB potato dextrose broth). After placing a (DMSO) solution of the test compounds into a microtiter plate (96-well format), the nutrient broth containing the fungal material is added. The test plates are incubated at 24° C. and the inhibition of growth is determined photometrically 3-4 days after application.

The following compounds give at least 80% control on *Thanatephorus cucumeris* at 200 ppm: 1, 2, 4, 5, 6, 8, 10, 12, 13, 20, 21, 22, 24, 26, 27, 28, 30, 36.

*Glomerella lagenarium* (*Colletotrichum lagenarium*)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

The following compounds give at least 80% control on *Glomerella lagenarium* at 200 ppm: 1, 2, 3, 4, 5, 6, 7, 8, 9, 10, 11, 12, 13, 14, 15, 16, 18, 19, 20, 21, 22, 23, 24, 25, 26, 27, 28, 30, 31, 32, 34, 35, 36.

*Fusarium culmorum*

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds give at least 80% control on *Fusarium culmorum* at 200 ppm: 1, 2, 3, 4, 5, 6, 8, 9, 10, 11, 12, 13, 15, 18, 20, 21, 22, 23, 24, 25, 26, 27, 28, 30, 31, 32, 36.

*Mycosphaerella arachidis* (*Cercospora arachidicola*)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds give at least 80% control on *Mycosphaerella arachidis* at 200 ppm: 1, 2, 3, 4, 5, 6, 7, 8, 9, 10, 11, 12, 13, 15, 16, 18, 19, 20, 21, 22, 23, 24, 25, 26, 27, 28, 30, 31, 32, 33, 34, 35, 36.

*Pythium ultimum*

Mycelia fragments and oospores of a newly grown liquid culture of the fungus are directly mixed into nutrient broth (PDB potato dextrose broth). After placing a (DMSO) solution of test compound into a microtiter plate (96-well format), the nutrient broth containing the fungal mycelia/spore mixture is added. The test plates are incubated at 24° C. and the inhibition of growth is determined photometrically 2-3 days after application.

The following compounds give at least 80% control on *Pythium ultimum* at 200 ppm: 1, 2, 3, 4, 5, 6, 7, 8, 9, 10, 11, 12, 13, 15, 18, 19, 20, 21, 22, 23, 24, 25, 26, 27, 28, 30, 31, 32, 36.

*Plasmopara viticola*

Grape vine leaf disks are placed on water agar in multiwell plates (24-well format) and sprayed with the formulated test compound diluted in water. The leaf disks are inoculated with a spore suspension of the fungus 1 day after application. The inoculated leaf disks are incubated at 19° C. and 80% rh under a light regime of 12 h light/12 h darkness in a climate cabinet and the activity of a compound is assessed as percent disease control compared to untreated when an appropriate level of disease damage appears in untreated check leaf disks (6-8 days after application).

The following compounds give at least 80% control on *Plasmopara viticola* at 200 ppm: 5, 15.

*Puccinia recondita*

Wheat leaf segments cv. Kanzler are placed on agar in multiwell plates (24-well format) and sprayed with the formulated test compound diluted in water. The leaf disks are inoculated with a spore suspension of the fungus 1 day after application. The inoculated leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (7-9 days after application).

The following compounds give at least 80% control on *Puccinia recondita* at 200 ppm: 39.

*Magnaporthe grisea* (*Pyricularia oryzae*)

Rice leaf segments cv. Ballila are placed on agar in a multiwell plate (24-well format) and sprayed with the formulated test compound diluted in water. The leaf segments are inoculated with a spore suspension of the fungus 2 days after application. The inoculated leaf segments are incubated at 22° C. and 80% rh under a light regime of 24 h darkness followed by 12 h light/12 h darkness in a climate cabinet and the activity of a compound is assessed as percent disease control compared to untreated when an appropriate level of disease damage appears in untreated check leaf segments (5-7 days after application). The following compounds give at least 80% control on *Magnaporthe grisea* at 200 ppm: 1, 2, 8, 12, 30.

*Phaeosphaeria nodorum* (*Septoria nodorum*)

Wheat leaf segments cv. Kanzler are placed on agar in a multiwell plate (24-well format) and sprayed with the formulated test compound diluted in water. The leaf disks are inoculated with a spore suspension of the fungus 2 days after application. The inoculated test leaf disks are incubated at 20° C. and 75% rh under a light regime of 12 h light/12 h darkness in a climate cabinet and the activity of a compound is assessed as percent disease control compared to untreated when an appropriate level of disease damage appears in untreated check leaf disks (5-7 days after application).

The following compounds give at least 80% control on *Phaeosphaeria nodorum* at 200 ppm: 8, 12, 30.

*Alternaria solani*

4-week old tomato plants cv. Roter Gnom are sprayed in a spray chamber with the formulated test compound diluted in water. The test plants are inoculated by spraying them with a spore suspension two days after application. The inoculated test plants are incubated at 22/18° C. (day/night) and 95% rh in a greenhouse and the percentage leaf area covered by disease is assessed when an appropriate level of disease appears on untreated check plants (5-7 days after application).

The following compounds give at least 60% control on *Alternaria solani* at 60 ppm: 1, 2, 3, 5, 7, 8, 14, 15, 18, 27, 28.

*Pyrenophora teres* (*Helminthosporium teres*)

1-week old barley plants cv. Regina are sprayed in a spray chamber with the formulated test compound diluted in water. The test plants are inoculated by spraying them with a spore suspension 2 days after application. The inoculated test plants are incubated at 20° C. and 95% rh and the percentage leaf area covered by disease is assessed when an appropriate level of disease appears on untreated check plants (5-7 days after application).

The following compounds give at least 60% control on *Pyrenophora teres* at 60 ppm: 1, 2, 28.

*Pythium ultimum* on Cotton/Pouch

Into each pouch 2 seeds of the respective test plant are sown. 9.5 ml compound solution are added at the same time. A spore/mycelium suspension is pipetted into the pouch simultaneously. After an incubation period of 7 days at 17° C. and 90% r. h. in a growth chamber the disease incidence was assessed.

The following compounds give at least 50% control on *Pythium ultimum* at 20 ppm: 1, 2, 4, 5, 7, 8, 9, 12.

*Puccinia recondita* on Wheat/Pouch

Into each pouch 15 seeds of the respective test plant are sown. 9.5 ml compound solution are added at the same time. 8 days after sowing wheat plants were inoculated by spraying a spore suspension on the test plants. After an incubation period of 8 days at 24° C./22° C. (day/night) and 80% rH in a growth chamber the disease incidence was assessed.

The following compounds give at least 50% control on *Puccinia recondita* at 20 ppm: 7.

*Fusarium culmorum* on Wheat/Pouch

Into each pouch 15 seeds of the respective test plant are sown. 9.5 ml compound solution are added at the same time. A spore suspension is pipetted into the pouch simultaneously. After an incubation period of 10 days at 5° C./22° C. and 90%/80% r. h. (5 d/5 d) in a growth chamber the disease incidence was assessed.

The following compounds give at least 50% control on *Fusarium culmorum* at 20 ppm: 5, 8, 12, 30.

*Monographella nivale* (syn. *Microdochium nivale*) on Wheat/Pouch

Into each pouch 15 artificially infected seeds of the respective test plant are sown. 9.5 ml compound solution are added at the same time. After an incubation period of 28 days at 5° C./17° C. and 90%/80% r. h. (21 d/7 d) in a growth chamber the disease incidence was assessed.

The following compounds give at least 50% control on *Monographella nivale* at 20 ppm: 8, 12, 24, 30.

*Pseudoperonospora cubensis* on Cucumber/Pouch

Into each pouch 2 seeds of the respective test plant are sown. 9.5 ml compound solution are added at the same time. 8 days after sowing cucumber plants were inoculated by spraying a spore suspension on the test plants. After an incubation period of 7 days at 24° C. and 95% r. h. in a growth chamber the disease incidence was assessed.

The following compounds give at least 50% control on *Pseudoperonospora cubensis* at 60 ppm: 5.

*Gäumannomyces graminis* on Wheat/Pouch

Into each pouch 15 seeds of the respective test plant are sown. 9.5 ml compound solution are added at the same time. A mycelium suspension is pipetted into the pouch simultaneously. After an incubation period of 15 days and 95%/80% r. h. (5 d/10 d) in a growth chamber the disease incidence was assessed.

The following compounds give at least 50% control on *Gäumannomyces graminis* at 20 ppm: 3, 4, 7, 10, 26.

Example B-1: Activity Against *Fusarium graminearum* on Maize

After application of the active ingredient formulated as a flowable concentrate for seed treatment onto maize seeds the seeds are sown in trays filled with soil artificially infested with *F. graminearum*. The trays are kept in a growth room for 3 weeks at 10° C. After this period the trial is transferred to a greenhouse where a temperature of 13° C. and a 14 h light period is provided. The following assessments are made 9 weeks after sowing: number of germinated plants. Each number is determined for 150 seeds per treatment (3 replicates a 50 seeds).

The following compounds give at least 80% control of *Fusarium graminearum* at a rate of 20 g/100 kg seeds: 1, 2, 5, 8, 12, 13, 30

Example B-2: Activity Against *Fusarium subglutinans* on Maize

After application of the active ingredient formulated as a flowable concentrate for seed treatment onto maize seeds infested with *F. subglutinans* the seeds are placed onto petri dishes filled with a layer of agar. The petri dishes are incubated in a climate cabinet for 6 days at 20° C. under a light regime of 12 h NUV-light/12 h darkness. The following assessments are made: percentage of *F. subglutinans* infected seeds. Each number is determined for 50 seeds per treatment (5 replicates a 10 seeds).

The following compounds give at least 80% control of *Fusarium sublutinans* at a rate of 20 g/100 kg seeds: 1, 2, 5, 8, 12, 13, 30

Example B-3: Activity Against *Monographella nivalis* (Syn. *Microdochium nivale*) on Wheat After application of the active ingredient formulated as a flowable concentrate for seed treatment onto *M. nivale*-infected seeds of winter wheat the seeds are sown in trays filled with planting soil. The trial is kept for 4 weeks in a growth room at 4° C. and darkness. Then the temperature is increased to 15° C. and a 12 h light period is provided. After development of the primary leaf plants are kept at 10° C. and high humidity until the trial is finished. The following assessments are made: number of infected plants. Each number is determined for 100 seeds per treatment (2 replicates a 50 seeds).

The following compounds give at least 50% control of *Monographella nivalis* at a rate of 20 g/100 kg seeds: 5, 8

Example B-4: Activity Against *Pyrenophora graminea* on Barley

After application of the active ingredient formulated as a flowable concentrate for seed treatment onto *P. graminea*-infected seeds of winter barley the seeds are sown in trays filled with field soil. The trays are kept in a growth room for 3 weeks at 4° C. After this period the trial is transferred to a greenhouse where a temperature of 12° C. and a 14 h light period is provided. The following assessments are made: number of infected plants. Each number is determined for 200 seeds per treatment (2 replicates a 100 seeds).

The following compounds give at least 80% control of *Pyrenophora graminea* at a rate of 20 g/100 kg seeds: 1, 2, 5, 8, 30

Example B-5: Activity Against *Pythium ultimum* on Cotton

After application of the active ingredient formulated as a flowable concentrate for seed treatment onto seeds of cotton the seeds are sown in trays filled with soil artificially infested with *P. ultimum*. The trial is kept for 1 week in a growth room at 20° C. and darkness. After this period the trial is transferred to a greenhouse where a temperature of 21° C. and a 14 h light period is provided until the trial is finished. The following assessments are made: number of germinated, healthy plants. Each number is determined for 150 seeds per treatment (3 replicates a 50 seeds).

The following compounds give at least 50% control of *Pythium ultimum* at a rate of 200 g/100 kg seeds: 1, 2, 5, 8, 10, 11, 12, 13, 26, 30

The invention claimed is:

1. A method for controlling infestation of plants or plant propagation material and/or harvested food crops susceptible to microbial attack by treating plants or plant propagation material and/or harvested food crops with an effective amount of an oxaborole of formula (Ic):

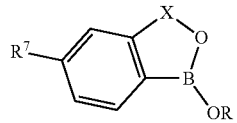

wherein $R^7$ is chlorine, X is $CH_2$ and R is H, $C_{1-4}$ alkyl optionally substituted by $-NR^3R^4$ wherein $R^3$ and $R^4$ are each independently, hydrogen, optionally substituted $C_{1-4}$-alkyl.

2. A method of controlling phytopathogenic diseases on plants or plant propagation material thereof according to claim 1, which comprises applying to said plant propagation material a fungicidally effective amount of a compound of formula (Ic).

3. A method according to claim 1, wherein plant propagation material of useful plants are seeds of useful plants.

4. A method of controlling phytopathogenic diseases on plants or plant propagation material thereof, which comprises applying to said plant propagation material a fungicidally effective amount of a plant propagation material protecting composition comprising a compound of formula (Ic) as defined in claim 1, together with a suitable carrier.

5. A plant propagation material comprising a compound of formula (Ic) as defined in claim 1.

6. A plant propagation material according to claim 5, which comprises additionally a colouring agent.

7. A method of protecting plant propagation material and organs that grow at a later point in time against damage of phytopathogenic diseases, which method comprises applying to said propagation material a fungicidally effective amount of a compound of formula (Ic) as defined in claim 1.

8. A coated plant propagation material wherein the coating comprises a compound of formula (Ic) as defined in claim 1.

9. A coated plant propagation material according to claim 8, wherein the said plant propagation material is a seed.

10. A product comprising a plant propagation material and a composition comprising a compound of formula (Ic) as defined in claim 1.

11. The product according to claim 10, wherein the said plant propagation material is a seed.

12. The product according to claim 10, further comprising a plant growth and/or seed germination medium.

* * * * *